United States Patent [19]

Berger

[11] 4,097,511

[45] Jun. 27, 1978

[54] ORGANOFUNCTIONAL-SILICON MATERIALS

[75] Inventor: Abe Berger, Schenectady, N.Y.

[73] Assignee: General Electric Company, Waterford, N.Y.

[21] Appl. No.: 843,214

[22] Filed: Jul. 18, 1969

Related U.S. Application Data

[63] Continuation-in-part of Ser. No. 691,928, Dec. 20, 1967.

[51] Int. Cl.$^2$ .......................... C07F 7/08; C07F 7/10; C07F 7/12
[52] U.S. Cl. ...................... 260/448.2 N; 260/448.2 B; 260/448.2 H
[58] Field of Search ..................... 260/448.2, 448.2 N, 260/448.2 B, 448.2 H

[56] References Cited

U.S. PATENT DOCUMENTS

| | | | |
|---|---|---|---|
| 3,168,544 | 2/1965 | Jex | 260/448.2 |
| 3,185,719 | 5/1965 | Prober | 260/448.2 |

*Primary Examiner*—Paul F. Shaver
*Attorney, Agent, or Firm*—E. Philip Koltos; Frank L. Neuhauser

[57] ABSTRACT

Organofunctional-silicon hydrides having, in addition, a halo substituent are provided. These compounds, of generic formula:

$$QSiYY'H, \qquad (1)$$

where Q is an organofunctional alkyl radical, Y is a halide radical, and Y' is Y or a monovalent hydrocarbon radical free of aliphatic unsaturation, are useful as intermediates in the production of various bis-(organofunctional-alkyl)silanes. Additionally, they are useful as waterproofing agents for various materials.

4 Claims, No Drawings

ORGANOFUNCTIONAL-SILICON MATERIALS

CROSS-REFERENCES TO RELATED APPLICATIONS

This application is a continuation-in-part of my co-pending application Ser. No. 691,928, filed Dec. 20, 1967, and entitled "Organofunctional-Silicon Materials."

A further related application is my copending application Ser. No. 691,930, filed Dec. 20, 1967, which describes and claims methods for forming the organofunctional-silicon hydrides.

BACKGROUND OF THE INVENTION

Bis-(organofunctional-alkyl)silanes are extremely useful. These materials can be employed, for example, in the preparation of solvent resistant organopolysiloxanes and are useful, in themselves, as glass sizings, fabric stiffeners, metal protectants, etc. Hitherto, these bis-(organofunctional-alkyl)silanes have been difficult to produce because of a lack of appropriate starting materials.

A valuable starting material for the production of bis-(organofunctional-alkyl)silanes is a silicon hydride which is, additionally, substituted with an organofunctional substituent and with a halogen substituent. If two halogen substituents are present, a dichlorosilane is produced which is useful in the formation of long chain organopolysiloxanes.

Further, the organofunctionally substituted silicon hydrides are useful, in themsleves, as waterproofing agents and for imparting improved surface properties to various substrates where bonding is achieved through the Si-H group.

SUMMARY OF THE INVENTION

The present invention relates to organofunctional-alkyl silicon hydrides of formula:

$$QSiYY'H, \qquad (1)$$

where Q is a radical selected from the class consisting of alkoxyalkyl, fluoroalkoxyalkyl, isocyanatoalkyl, organothioalkyl, and $$CNCH_2\underset{R'}{C}H-, \quad YCH_2\underset{R'}{C}HCH_2, \quad \text{and} \quad RSO_2CH_2\underset{R'}{C}H(CH_2)_a;$$

where Y is a halogen radical; R is a monovalent hydrocarbon radical free of aliphatic unsaturation; R' is selected from the class consisting of hydrogen and lower alkyl radicals of from 1 to 4 carbon atoms; Y' is selected from Y and R; and a is an integer from 1 to 5.

The organofunctional-silicon hydrides having a halo substituent, as shown in formula (1), can be formed by a redistribution reaction between a higher alkylsilicontrihydride and an organofunctional halosilane, where that organofunctional group is the one desired on the finally formed organofunctional-silicon hydride. This reaction is carried out in the presence of a tertiary amine catalyst by heating at elevated temperature, preferably under an inert atmosphere. The reaction can be represented by the following equation:

$$QSiY_2Y' + R''SiH_3 \xrightarrow{\text{amine}} QSiYY'H + R''SiH_2Y. \qquad (2)$$

The desired organofunctional-silicon hydride is generally removed from the reaction mixture by distillation.

DESCRIPTION OF THE PREFERRED EMBODIMENTS

As previously disclosed, the organofunctional-silicon hydrides of the present invention have the formula:

$$QSiYY'H, \qquad (1)$$

where Q is a monovalent radical selected from the class consisting of alkoxyalkyl, fluoroalkoxyalkyl, isocyanatoalkyl, organothioalkyl, and $$CNCH_2\underset{R'}{C}H-, \quad YCH_2\underset{R'}{C}HCH_2, \quad \text{and} \quad RSO_2CH_2\underset{R'}{C}H(CH_2)_a;$$

Y is a halide radical; R is a monovalent hydrocarbon radical free of aliphatic unsaturation; R' is selected from the class consisting of hydrogen and lower alkyl radicals having from 1 to 4 carbon atoms; Y' is selected from Y and R; and a is an integer of from 1 to 5.

Included among the radicals represented by R are, for example, aryl radicals, such as, phenyl, tolyl, xylyl, naphthyl, etc.; alkyl radicals, such as, methyl, ethyl, propyl, butyl, amyl, etc.; cycloalkyl radicals, such as, cyclopentyl, cyclohexyl, cycloheptyl, etc. Those substituents represented by R' include, for example, hydrogen, methyl, ethyl, propyl, and butyl.

Included broadly, among the organofunctional-silicon hydrides of formula (1) are, for example, cyanoalkylhalosilanes, alkoxyalkylhalosilanes, fluoroalkoxyalkylhalosilanes, isocyanatoalkylhalosilanes, organothioalkylhalosilanes, organosulfonylalkylhalosilanes, and haloalkylhalosilanes. More specifically, the organofunctional-silicon hydrides include such materials as:

cyanoalkyl silicon hydrides, such as:

$$NCCH_2CH_2SiCl_2H,$$

$$NCCH_2\underset{CH_3}{C}HSi(Cl)_2H,$$

etc.

organosulfonyl silicon hydrides, such as:
$$CH_3SO_2CH_2CH_2SiCl_2H,$$

$$C_6H_5SO_2CH_2CH_2CH_2SiCl_2H,$$

$$CH_3SO_2CH_2CH_2Si(Cl)(CH_3)H,$$

$$CH_3SO_2CH_2\underset{CH_3}{C}HCH_2SiCl_2H,$$

etc.

haloalkyl silicon hydrides, such as:

$$ClCH_2CH_2CH_2SiCl_2H,$$

$$ClCH_2CH_2CH_2Si(Cl)(CH_3)H,$$

$$ClCH_2\underset{CH_3}{C}HCH_2Si(Cl)_2H,$$

$$BrCH_2CH_2CH_2SiCl_2H,$$

etc.
   isocyanato silicon hydrides, such as:

$OCNCH_2CH_2CH_2SiCl_2H$, $OCNCH_2CH_2CH_2Si(Cl)(CH_3)H$, $OCNCH_2CH_2CH_2SiCl_2H$, etc.
   and organothio silicon hydrides, such as:

$CH_3SCH_2CH_2SiCl_2H$, $CH_3SCH_2CH_2Si(Cl)(CH_3)H$, $CH_3SCH_2CH_2CH_2SiCl_2H$, $C_6H_5SiCH_2CH_2SiCl_2H$, etc.

The method for forming these organofunctional-silicon hydrides having a halo substituent are taught in my copending application Ser. No. 691,930, filed concurrently with the parent of this application, and assigned to the same assignee as the present invention. As taught in the copending application, the organosilicon hydrides are formed by a redistribution reaction involving a corresponding organofunctional-silicon halide. This redistribution reaction is between the organofunctional halosilane and a higher alkylsilicontrihydride and the reaction is carried out in the presence of a tertiary amine catalyst at an elevated temperature.

In order that those skilled in the art may be better able to practice the present invention, the following examples are given by way of illustration, and not by way of limitation. All parts in these examples, except as otherwise indicated, are by weight.

EXAMPLE 1

A mixture of 3 moles of 3-trichlorosilylpropionitrile, 1 mole of dodecylsilane, and 8 mole percent of N,N,N',N'-tetramethylethylenediamine, the latter based upon the total reaction mixture, was heated in the presence of a nitrogen atmosphere at 130° C. for 5 hours. The mixture was fractionally distilled and the product boiling at 65° C. and 5 mm. pressure was collected. Based upon the method of preparation, the product was cyanoethyldichlorosilane of formula:

$$CNCH_2CH_2SiCl_2H. \qquad (3)$$

The yield was 80%, based upon the theoretical.

EXAMPLE 2

A mixture consisting of 218 parts of trichlorosilylpropylisocyanate, 66 parts of dodecylsilane, and 10.1 parts of triethylamine was heated for 5 hours at 130° C., under a nitrogen atmosphere. The mixture was fractionally distilled and the portion boiling at 62°–63° C. at 2 mm. pressure was collected. Based upon the method of preparation, the product was dichlorosilylpropylisocyanate of formula:

$$OCNCH_2CH_2CH_2SiCl_2H. \qquad (4)$$

The structure of this product was substantiated by infrared analysis. The yield of the product was 45%, based upon the theoretical.

EXAMPLE 3

A mixture of 2 moles of chloropropyltrichlorosilane, 1 mole of hexylsilane, and 7 mole percent, based upon the total, or tributylamine, was heated at 130° C. for 3 hours under an inert atmosphere. A sample of the mixture, after the 3 hour heating period, was analyzed by vapor phase chromatography and found to consist, principally, of chloropropyldichlorosilane and hexyldichlorosilane. The remaining mixture was fractionated and 28 parts of product boiling at 42°–46° C. at 60 mm. pressure was collected. Based upon the method of preparation, the product was gamma-chloropropyldichlorosilane of formula:

$$ClCH_2CH_2CH_2SiCl_2H. \qquad (5)$$

The yield represented 80%, based upon the theoretical.

EXAMPLE 4

A mixture consisting of 36.4 parts of cyanopropylmethyldichlorosilane, 24.7 parts of octadecylsilane, and 5 parts of tributylamine, was heated for 5 hours at 140° C. under an inert atmosphere. The reaction mixture was then fractionally distilled and the portion boiling at 75°–85° C. at 1 mm. pressure was collected. Based upon the method of preparation, the product was gamma-cyanopropylmethylchlorosilane of formula:

$$CNCH_2CH_2CH_2SiCH_3(Cl)H. \qquad (6)$$

The structure of this product was substantiated by its infrared spectrum. The amount collected represented a 45% yield, based upon the theoretical.

EXAMPLE 5

A mixture of 2 moles of chloropropyltrichlorosilane, 1 mole of hexylsilane, and 7 mole percent of tributylamine, based upon the total moles in the mixture, was heated at 130° C. for 3 hours under an inert atmosphere. A sample of the reaction mixture was then removed and analyzed by vapor phase chromatography. The chromatograph indicated a mixture, primarily, of chloropropyldichlorosilane and hexyldichlorosilane. The reaction mixture was then fractionally distilled and 28 parts of a product boiling at 42°–46° C. at 60 mm. pressure was collected. Based upon the method of preparation, the product was gamma-chloropropyldichlorosilane of formula:

$$ClCH_2CH_2CH_2SiCl_2H. \qquad (7)$$

The yield represented 80%, based upon the theoretical.

EXAMPLE 6

A mixture consisting of 3 moles of 2-methyl-3-chloropropyltrichlorosilane, 1 mole of octadecylsilane, and 8 mole percent of tri-n-butylamine, based upon the total of reactants, was heated for 5 hours at 120° C. under a nitrogen atmosphere. The reaction mixture was then fractionally distilled and the product boiling at 46°–55° C. at 4.6 mm. pressure was collected. Based upon the method of preparation, the product was 2-methyl-3-chloropropyldichlorosilane of formula:

$$ClCH_2\underset{CH_3}{\underset{|}{C}H}CH_2SiCl_2H. \qquad (8)$$

The structure of this product was substantiated by infrared analysis. The yield represented 70%, based upon the theoretical.

EXAMPLE 7

A mixture of 3 moles of 1-methyl-cyanoethyltrichlorosilane, 1 mole of dodecylsilane, and 8 mole percent of tributylamine, based upon the total of the reactants, was heated for 5 hours at 120° C. under an inert atmosphere. The mixture was fractionally distilled to obtain 65%, based upon the theoretical, of a product having the formula:

$$CNCH_2\underset{\underset{CH_3}{|}}{C}HSiCl_2H. \quad (9)$$

These examples are thus representative of a broad class of organofunctional-silicon hydrides having a halide substituent, as described by formula (1).

What I claim as new and desire to secure by Letters Patent of the United States is:

1. Organofunctional-silicon hydrides having the formula:

QSiYY'H, where Q is a monovalent radical selected from the class consisting of alkoxyalkyl, fluoroalkoxyalkyl, isocyanatoalkyl, methylthioalkyl, phenylthioalkyl, $$YCH_2\underset{\underset{R'}{|}}{C}HCH_2 \text{ and } RSO_2CH_2\underset{\underset{R'}{|}}{C}H(CH_2)_a;$$

R is a monovalent hydrocarbon radical free of aliphatic unsaturation; R' is selected from the class consisting of hydrogen and a lower alkyl radical of from 1 to 4 carbon atoms; Y is a halide radical; Y' is selected from the class consisting of Y and R; and $a$ is an integer of from 1 to 5.

2. The organofunctional-silicon hydride of claim 1 having the formula:

OCNCH$_2$CH$_2$CH$_2$SiCl$_2$H.

3. The organofunctional-silicon hydride of claim 1 having the formula:

ClCH$_2$CH$_2$CH$_2$SiCl$_2$H.

4. The organofunctional-silicon hydride of claim 1 having the formula:

$$ClCH_2\underset{\underset{CH_3}{|}}{C}HCH_2SiCl_2H.$$

* * * * *

UNITED STATES PATENT AND TRADEMARK OFFICE
CERTIFICATE OF CORRECTION

PATENT NO. : 4,097,511
DATED : June 27, 1978
INVENTOR(S) : Abe Berger

It is certified that error appears in the above—identified patent and that said Letters Patent is hereby corrected as shown below:

The term of this patent subsequent to April 27, 1989 has been disclaimed.

Signed and Sealed this

Fourth Day of March 1980

[SEAL]

Attest:

SIDNEY A. DIAMOND

Attesting Officer

Commissioner of Patents and Trademarks